Nov. 27, 1956 L. LENS Plant Pat. 1,530
ROSE PLANT
Filed Jan. 5, 1956
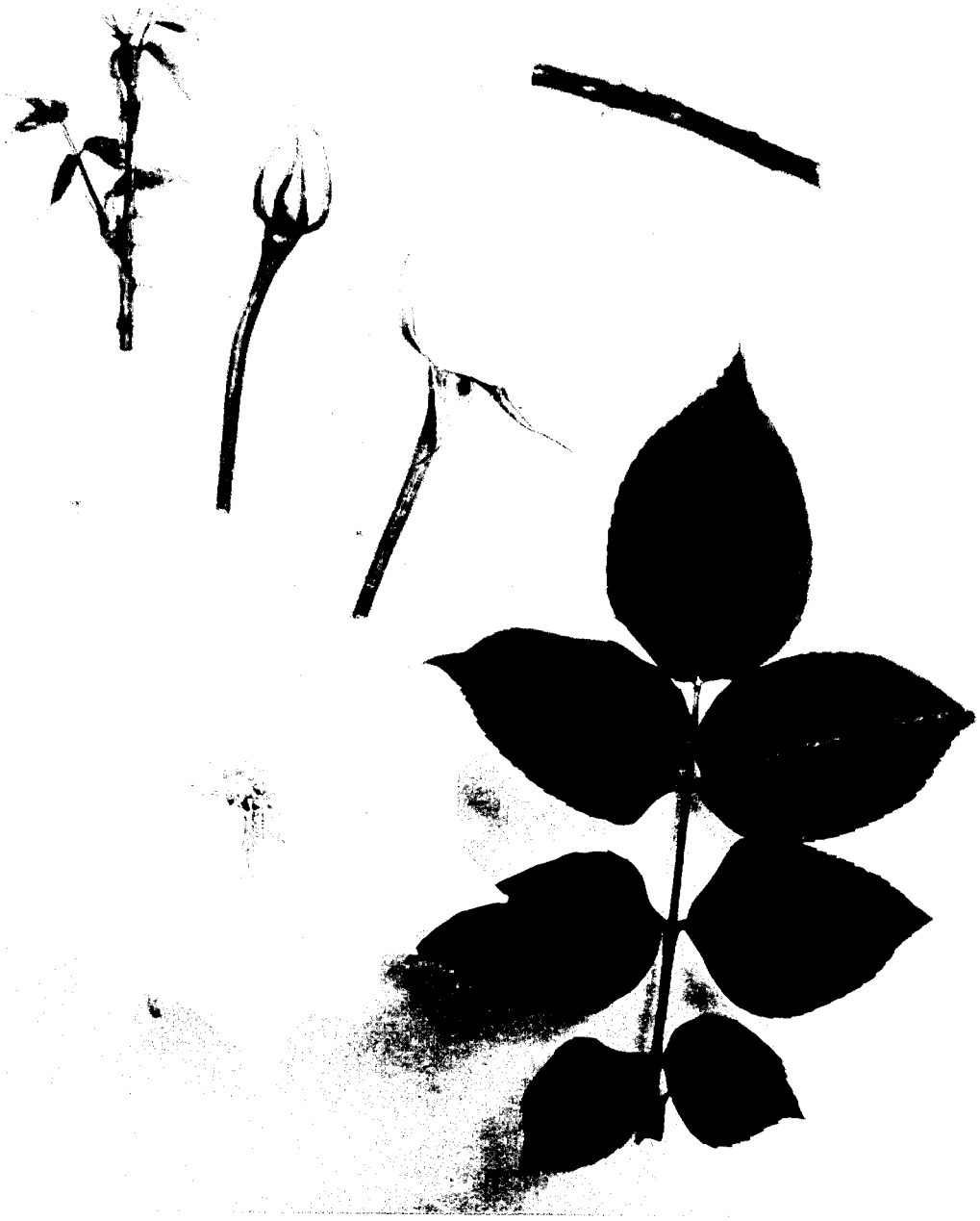
Inventor.
Louis Lens
By: Robert Cobb
Attorneys.

United States Patent Office

Plant Pat. 1,530

Patented Nov. 27, 1956

1,530

ROSE PLANT

Louis Lens, Wavre-Notre-Dame, Belgium, assignor to Jackson & Perkins Company, Newark, N. Y., a corporation of New York Application January 5, 1956, Serial No. 557,617

1 Claim. (Cl. 47—61)

The present invention relates to a new and distinct variety of rose plant of the hybrid tea class, which was originated by me by crossing the variety "Lady Sylvia" (unpatented) with an unnamed and unpatented seedling derived from "Virgo" (unpatented) × "White Briarcliff" (Plant Patent No. 108).

The primary objective of this breeding was to produce a new white rose variety having improved heavy flower petals and which is suitable for both cut flower and out-of-door use. This objective was fully achieved, along with other characteristics representing a unique combination of features in a rose of this class, as evidenced by the following characteristics which are predominant in the new variety:

(1) The upright and firm plant growth;

(2) The heavy, stiff petals of the flowers, which are quite unusual in white hybrid tea varieties;

(3) The floriferousness of the variety and the suitability of the flowers for both cut flower and out-of-door use; and (4) The distinctive and attractive white color of the flowers.

The foregoing characteristics definitely differentiate my new variety from its parents, as well as from all other varieties of its class of which I am aware, and asexual reproduction of the new variety by budding, as performed at Newark, New York, U. S. A., and also at Pleasanton, California, U. S. A., shows that the aforementioned characteristics and distinctions come true to form and are established and transmitted through succeeding propagations.

The accompanying drawing shows typical specimens of the vegitative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—"Lady Sylvia."

*Pollen parent.*—An unnamed seedling derived from crossing "Virgo" × "White Briarcliff."

Classification:

*Botanic.*—Hybrid tea.

*Commercial.*—Hybrid tea.

FLOWER (Observations made from specimens grown in a greenhouse at Newark, New York, U. S. A., in the latter part of the month of July and about mid-morning.)

Blooming habit: Recurrent—continuous.

Bud:

*Size.*—Large.

*Form.*—Ovoid; is not affected by wet or hot weather.

*Color.*—When sepals first divide—Glass Green, Plate 31. When petals begin to unfurl—Pale Lumiere Green, Plate 17. When half-blown:—inside of petals—White, Plate 53, lightly overcast with Seafoam Yellow, Plate 31; reverse of petals—White, Plate 53, lightly overcast with Pale Glass Green, Plate 31.

*Sepals.*—Slightly branched; curl back when petals begin to unfurl. Color—Inside—Kildare Green, Plate 31. Outside—Spinach Green, Plate 5.

*Calyx.*—Color—Spinach Green, Plate 5. Shape—funnel. Size—small. Aspect—smooth. Odor when rubbed—none.

*Peduncle.* — Length — long. Aspect — rough. Strength—stiff; heavy. Color—Light Bice Green, Plate 17.

*Opening.*—Opens up well; is not affected by adverse weather conditions.

Bloom:

*Size.*—Large. Average size when fully expanded—from 4½ inches to 5 inches.

*Flowers borne.*—Singly.

*Stems.*—Medium length; strong.

*Form* (when first open).—High center. Permanence—retains its form to the end; outer petals curl back.

*Petalage.*—Double (full but open center). Number of petals under normal conditions—25.

*Color.*—Center of flower—White, Plate 53, lightly overcast with Citron Yellow, Plate 16. Outer petals—White, Plate 53. Base of petals (aiglet)—Citron Yellow, Plate 16. Inside of petals—White, Plate 53. Reverse of petals—White, Plate 53. General tonality from a distance—White, Plate 53.

*Discoloration.*—General tonality at end of first day—White, Plate 53. Second day—White, Plate 53. Third day—White, Plate 53.

Petals:

*Texture.*—Leathery and stiff; is not affected by wet or hot weather.

*Appearance.*—Inside—shiny; outside—shiny.

*Form.*—Round; slightly notched.

*Arrangement.*—Imbricated (regularly arranged shingle-like).

*Petaloids in center.*—Few; large.

*Persistence.*—Drop off cleanly.

*Fragrance.*—Moderate. Nature—"Old Rose perfume" (Centifolia).

*Lasting quality.*—On the plant—very long; as cut flower—very long.

GENITAL ORGANS

Stamens, Anthers: Large; many; regularly arranged around styles. Color—Light Orange Yellow, Plate 3.

Stamens, Filaments (threads): Medium length. Color—Pinard Yellow, Plate 4.

Pollen: Color—Baryta Yellow, Plate 4.

Styles: Bunched; uneven length; short; thin.

Stigmas: Color—Amber Yellow, Plate 16.

Ovaries: All enclosed in calyx.

Hips: None.

Seeds: None.

PLANT

Form: Bush.

Growth: Vigorous; firm; upright.

Foliage: Compound of 5 to 7 leaflets.

*Size.*—Large.

*Quantity.*—Abundant.

*Color.*—New foliage: Upper side — Cosse Green, Plate 5, with serrations of Carmine, Plate 1; Under side—Oil Green, Plate 5, lightly overcast with Tawny Olive, Plate 29. Old foliage: Upper side—Dark Cress Green, Plate 31; under side—Light Cress Green, Plate 31.

*Shape.*—Oval pointed.

*Texture.*—Upper side—leathery; under side—smooth.

*Ribs and veins.*—Ordinary.

*Edge.*—Serrated (saw-toothed).

*Serration.*—Both double and single; small.

*Leaf stem.*—Color—Light Elm Green, Plate 17. Under side—smooth.

*Stipules.*—Medium length; smooth.

Wood:

*New wood.*—Color—Parrot Green, Plate 6. Bark—smooth.

*Old wood.*—Color—Dark Cress Green, Plate 31. Bark—smooth.

Thorns:

*Thorns.*—Quantity: On main stalks from base—many; on laterals from stalk—ordinary. Form— medium length; hooked downward; with narrow base. Color (when young)—Carrot Red, Plate 14. Position—irregular.

*Prickles.*—Quantity: On main stalks—none; on laterals—none.

*Short needles.*—Quantity: On main stalks—none; on laterals—none.

I claim:

A new and distinct variety of rose plant of the hybrid tea class, substantially as herein shown and described, characterized particularly as to novelty by its upright and firm growth, its stiff-petaled flowers, it floriferousness and suitability for both cut flower and out-of-door use, and the distinctive white color of its flowers.

No references cited.